United States Patent
Rodrigues et al.

(10) Patent No.: US 9,126,967 B2
(45) Date of Patent: Sep. 8, 2015

(54) PROCESS FOR THE PRODUCTION OF A DIOXOLANE COMPOUND FROM CRUDE GLYCEROL

(75) Inventors: Edson Rodrigues, Pirassununga (BR); Arthur Malheiro, Araraquara (BR)

(73) Assignee: RHODIA POLIAMIDA E ESPECIALIDADES LTDA, Sao Paulo (BR)

( * ) Notice: Subject to any disclaimer, the term of this patent is extended or adjusted under 35 U.S.C. 154(b) by 0 days.

(21) Appl. No.: 14/347,262

(22) PCT Filed: Sep. 30, 2011

(86) PCT No.: PCT/IB2011/002302
§ 371 (c)(1),
(2), (4) Date: Mar. 27, 2014

(87) PCT Pub. No.: WO2013/045968
PCT Pub. Date: Apr. 4, 2013

(65) Prior Publication Data
US 2014/0235878 A1    Aug. 21, 2014

(51) Int. Cl.
*C07D 317/00* (2006.01)
*C07D 317/20* (2006.01)

(52) U.S. Cl.
CPC ................... *C07D 317/20* (2013.01)

(58) Field of Classification Search
CPC .................................................. C07C 29/92
USPC ................................. 568/869; 549/453
See application file for complete search history.

(56) References Cited

U.S. PATENT DOCUMENTS 4,060,532 A  * 11/1977 Hartmann .................. 549/452
2011/0112336 A1    5/2011 Macret et al.

FOREIGN PATENT DOCUMENTS

| EP | 1 905 767 | * | 4/2008 | ........... 568/869 |
| GB | 933714 | * | 8/1963 | ........... 56/869 |
| WO | WO 2009/141702 | * | 11/2009 | ........... 568/869 |
| WO | WO2012034905 A1 | | 3/2012 | |
| WO | WO2013045967 A1 | | 4/2013 | |

OTHER PUBLICATIONS

Hill et al, Carbohydrates and Polysaccharides XV (1928), pp. 2235-2242.*
Gemma, V. et al.,—"Acetalisation of bio-glycerol with acetone to produce solketal over sulfonic mesostructured silicas" Green Chemistry (2010) vol. 12, pp. 899-907—XP55027956 (10 pages).
Fessenden, R. J. & Fessenden, J. S.—Section 11.8 "Reaction with Alcohols" in Chapter 11 "Aldehydes and Ketones" in Book: *Organic Chemistry*, 2nd Edition (1982), PWS Publishers, pp. 522-525 (6 pages).
Green, T.—section entitled "Protection for 1,2- and 1,3-diols" in Chapter 2: "Protection for the Hydroxyl Group Including 1,2- and 1,3-Diols" of Book: *Protective Groups in Organic Chemistry*, John Wiley & Sons (1981), pp. 72-86 (20 pages).
U.S. Appl. No. 14/347,249, Edson Rodrigues et al., filed Mar. 26, 2014.

* cited by examiner

*Primary Examiner* — Andrew D Kosar
*Assistant Examiner* — Raymond Covington
(74) *Attorney, Agent, or Firm* — Xuping Fu

(57) ABSTRACT

A process for the production of dioxolane compounds of formula (I):

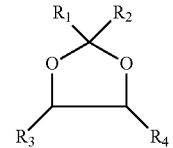

wherein R1 and R2 independently represent hydrogen or an alkyl chain from 1 to 10 carbon atoms; R3 and R4 independently represent hydrogen, an alkyl chain from 1 to 5 carbon atoms, or an alkyl chain from 1 to 5 carbon atoms which is endowed with one or more hydroxyl groups, such process comprising a reaction between crude glycerol and an aldehyde or a ketone, with a molar ratio of aldehyde:glycerol or ketone:glycerol from 3:1 to 20:1.

18 Claims, 1 Drawing Sheet

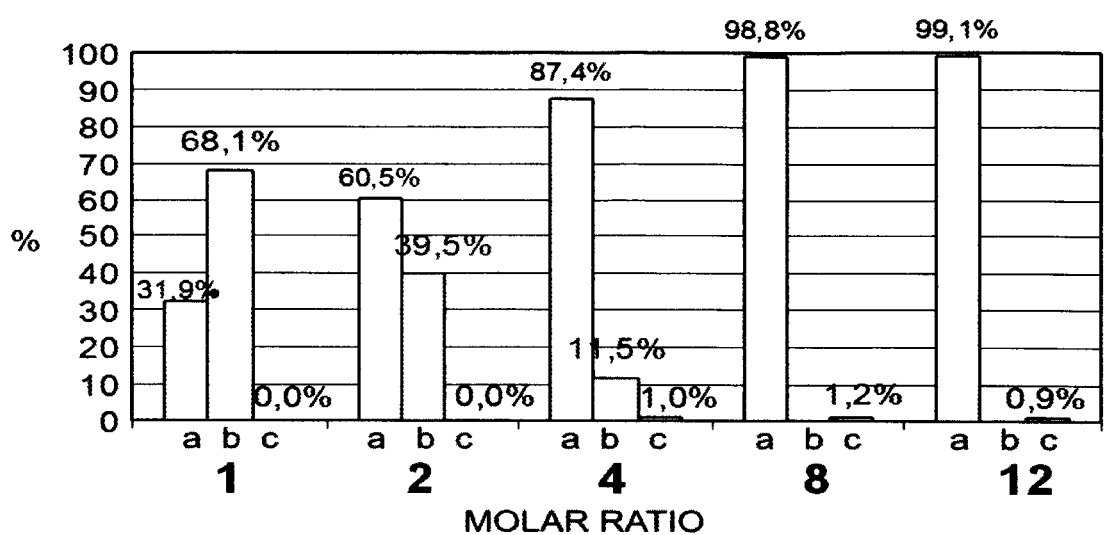

PROCESS FOR THE PRODUCTION OF A DIOXOLANE COMPOUND FROM CRUDE GLYCEROL

CROSS-REFERENCE TO RELATED APPLICATIONS

The present application is a U.S. national stage entry under 35 U.S.C. §371 of International Application No. PCT/IB2011/002302 filed Sep. 30, 2011.

TECHNICAL FIELD OF THE INVENTION

The present invention concerns a process for the production of dioxolane compounds comprising the reaction between crude glycerol and aldehydes or ketones, under conditions with which most chlorides become insoluble and are easily withdrawn from the reaction medium.

BACKGROUND ART

Crude glycerol Crude glycerol is a by-product of the process to obtain biodiesel, namely a transesterification of vegetable raw material, such as natural oils or animal fat, with lower alcohols.

Such a transesterification process is the method most often employed to enable the use of vegetable oils (for instance coconut, soy, castor, sunflower, peanut) and animal fat as fuel, for instance in the presence of a homogeneous or heterogeneous alkaline catalyst.

From the transesterification reaction in a basic or acid medium, one obtains a monoalkyl ester—the biodiesel fuel—and glycerol.

A general equation for that reaction would be: triglyceride+3 alkyl alcohol→glycerol+3 fatty acid alkyl ester The monoalkyl ester and the glycerol formed in the transesterification reaction are substantially immiscible and are separated by decantation at the end of the reaction.

Very commonly, in that process to obtain biodiesel, the neutralization of the transesterification product with hydrochloric acid gives origin to a sodium chloride contamination solubilized in the decanted glycerin. The presence of sodium chloride accelerates corrosion in stainless steel equipment.

This raw glycerol, byproduct of the transesterification reaction, has low purity and contains, among several contaminants, fatty acids, fatty acid salts, inorganic salts, inorganic acids, inorganic bases, water, lower alcohols, mono-, di- and triglycerides, esters of fatty acids with lower alcohols, transesterification catalyst residue, etc. To enable the use of this raw glycerol, the traditional path has been the removal of its contaminants with several purification steps, to obtain a purer product commonly referred to as blond glycerin, which is then bi-distilled, to reach high purity. It is obviously a long and costly process when compared to the use of the crude glycerol.

Dioxolane and Process to Obtain It

Dioxolanes, in the sense utilized herein, are a group of organic compounds containing the 1,3-dioxolane ring, known to be used in several applications, such as pharmaceutical actives, chemical intermediates and solvents. The particular use as solvent is interesting as it is less harmful than traditional solvents, with similar performance.

The preparation of a dioxolane compound by way of reacting glycerol and a ketone or an aldehyde is generally known, for instance as in the following publications: R. J. Fessenden & J. F. Fessenden, Organic Chemistry, 2nd edition, page 524, 1982 and T. W. Greene, Protective Groups in Organic Chemistry, John Wiley & Sons, 1981. No mention to the use of crude glycerol and the effects of the contaminants upon the reaction is mentioned.

SUMMARY OF THE INVENTION

The present invention concerns a process for the production of dioxolane compounds of formula (I):

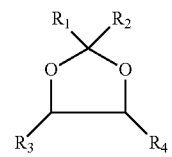

comprising a reaction between crude glycerol and aldehyde or ketone, with a molar ratio of aldehyde:glycerol or ketone: glycerol from 3:1 to 20:1, where R1 and R2 independently represent hydrogen or an alkyl chain from 1 to 10 carbon atoms, more particularly an alkyl chain from 1 to 5 carbon atoms, for instance methyl, ethyl, propyl, isopropyl, butyl, isobutyl, pentyl and isopentyl; and R3 and R4 independently represent hydrogen, an alkyl chain from 1 to 5 carbon atoms, or an alkyl chain from 1 to 5 carbon atoms which is endowed with one or more hydroxyl groups.

In the reaction between crude glycerol and aldehyde, one of the groups R1 and R2 is hydrogen. In the reaction between glycerol and ketone, the groups R1 and R2 do not represent hydrogen.

BRIEF DESCRIPTION OF THE DRAWING

FIG. 1 represents weight percents of three fractions obtained by decantation of a reaction medium after reaction between crude glycerol and acetone with respect to various acetone:glycerol molar ratios according to an embodiment of the present invention.

DETAILED DESCRIPTION

Without excluding any other, adequate ketones employed in the reaction with glycerol are acetone, cyclohexanone, methyl cyclohexanone, methyl cyclopentanone, methyl isobutyl ketone, 4-hydroxy-4-methyl-2-pentanone, 2-butanone, 3-butanone, diisobutyl ketone, 4-methyl-3-penten-2-one, 2-nonanone, 2-pentanone, 3-methyl-2-butanone and 1-phenylethanone and mixtures thereof. Preferably, the ketone is acetone.

Without excluding any other, adequate aldehydes employed in the reaction with glycerol are formaldehyde, acetaldehyde, 2-ethylhexanal and furfuraldehyde and mixtures thereof.

In a particular embodiment of the invention, it is possible to utilize one or more ketones and/or aldehydes to react with the crude glycerol. According to the invention, crude glycerol advantageously reacts with ketone and most advantageously with acetone.

The dioxolane compounds obtained by the invention are acetals or ketals. The acetals are obtained by nucleophilic addition of an alcohol to an aldehyde in acidic conditions, followed by elimination of water. The ketals are obtained by the same type of reaction performed with ketones.

Without excluding any other, particular 1,3-dioxolanes obtained by the invention are 2-hydrocarbyl-1,3-dioxolane-4-methanol, for instance:

2,2-dimethyl-1,3-dioxolane-4-methanol
2,2-diisobutyl-1,3-dioxolane-4-methanol
2-isobutyl-2-methyl-1,3-dioxolane-4-methanol
2-butyl-2-ethyl-1,3-dioxolane-4-methanol
2-phenyl-1,3-dioxolane-4-methanol According to the invention, a preferred dioxolane resulting from the reaction step of the invention between glycerol and acetone is 2,2-dimethyl-1,3-dioxolane-4-methanol, also known as solketal.

According to the invention, the molar ratio of aldehyde:glycerol or ketone:glycerol is comprised from 3:1 to 20:1, preferably from 4:1 to 15:1, more preferably from 6:1 to 12:1.

It was verified that, within the above-mentioned molar ratio range, the insolubilization of the chlorides is optimized, what makes their withdrawal from the reaction medium—for instance by decantation or filtration—more effective than with other molar ratios. In other words, outside those limits, a larger amount of the chlorides remains solubilized in the reaction medium, therefore not as easily separable. As a consequence, because of the lesser presence of chlorides, the equipment associated with the reaction vessel, such as distillation columns, do not need to be particularly resistant to corrosion.

Particular embodiments of the reaction comprised in the process of the invention, not excluding any other alternative, is adequately performed according to one or more of the following parameters:

temperature: between 10 and 60° C., preferably between 20 and 45° C.;
pressure: atmospheric;
catalyst: acid, such as sulfuric acid, metanesulfonic acid, xylenesulfonic acid, acetic acid, adequate amounts of catalyst are 0,2 to 1% weight in relation to the weight of glycerol;
alkalinity: between 0.04 and 10 mg KOH/g, in particular from 0.08 to 1.8 mg KOH/g of glycerol;
duration: 30 min to 5 hours, preferably 1 to 2 hours;
solvent: none or organic solvents like heterocyclic and aromatic organic compounds. Among heterocyclic and aromatic organic compounds, furan compounds are preferred, for example Tetrahydrofuran (THF) and 2-Methyltetrahydrofuran (2MeTHF);
crude glycerol: as such, preferably obtained as a by-product of the process for producing biodiesel, namely a transesterification of vegetable raw material, such as natural oils or animal fat, with lower alcohols. Crude glycerol advantageously contains glycerol from 40 to 95%, particularly from 75 to 90% by weight, water from 1 to 15%, preferably from 5 to 15% by weight, inorganic salts, especially chlorides, from 1 to 15%, preferably from 5 to 15% by weight and other organic impurities like free fatty acids, salts of fatty acids, esters, sulfur compounds, proteins and minerals). Crude glycerol is advantageously previously dehydrated, for instance under vacuum, at 70-80° C., so that the content of water is lower than 5% by weight.

In a particular embodiment, the invention concerns a process for the production of dioxolane compounds of formula (I) characterized by the fact that it comprises the following steps:

a)—in a reaction vessel, reacting crude glycerol and ketone or aldehyde, with a molar ratio of aldehyde:glycerol or ketone:glycerol from 3:1 to 20:1, preferably from 4:1 to 15:1, more preferably from 6:1 to 12:1;

b)—allowing decantation, then separating solids, the remaining liquid fraction presenting a light phase and a heavy phase;

c)—removing salt from said heavy phase, the remaining portion thereof being optionally returned to the reaction vessel;

d)—subjecting said light phase to distillation to separate the dioxolane compound from ketone or aldehyde, which are optionally recycled to the reaction vessel;

e)—subjecting the obtained dioxolane compound to a further distillation to remove water.

The step a) is carried out in a reaction vessel according to the operating conditions given above. A dehydration of the crude glycerol is preferentially performed prior to step a).

The light phase rich in dioxolane, aldehyde or ketone, presents a chloride content in the range 0.005-0.8% wt, preferably 0.01-0.40% wt, more preferably 0.01-0.20 and even more preferably 0.05-0.20 while the heavy phase contains mainly glycerol, fatty salts, sodium chloride and water. Step b) is preferably carried out during 30 minutes to 2 hours.

Adequate removal means on step c) are filtration and centrifugation, alone or in combination.

A dehydration of the crude glycerol, prior to step a), may optionally be performed, for instance under vacuum of about $9 \times 10^3$-$14 \times 10^3$ Pa and temperature 70-80° C.

The distillation in step d) may be adequately performed in an atmospheric column with temperatures in the range of 60 to 90° C.

The distillation in step e may be adequately performed under vacuum, for instance $1 \times 10^3$-$3 \times 10^3$ Pa, and temperatures in the range of 110-120° C.

A neutralization step with alkali, for instance sodium hydroxide, may optionally be performed between steps a) and b), and/or between steps b) and c). Adequate amounts of neutralizing alkali are chosen so that the reaction medium reaches an alkalinity between 0.1 and 0.5 mg KOH/g, in particular from 0.2 to 0.3 mgKOH/g of glycerol.

The light phase, before step d), may optionally be subjected to contact with basic resin, activated carbon or a silica system, and separation, to further lower level of sodium chloride, for instance below 10 ppm of chloride.

EXAMPLE

The following example is given only as a particular embodiment of the invention, in no way imposing limitations beyond the contents of the claims presented further on.

Crude glycerol (alkalinity 5.9 mg KOH/g) corresponding to the composition below was used as starting material for the reaction comprised in the invention (percentages in weight):

glycerol 78.40%
chloride 6.42%
water 11.52%
impurities 3.66%

Acetone was used to react with the crude glycerol.

The catalyst was sulfuric acid, 0.5% in weight with relation to the weight of glycerol.

The reaction was performed at 40° C. for 2 hours.

Decantation was allowed for 1 hour at 35-40° C., with the liquid portion showing the separation of a top light phase from a bottom heavy phase.

Tested molar ratio acetone:glycerol were: 1:1; 2:1; 4:1; 8:1 and 12:1.

Results

The dioxolane obtained by the reaction described above was solketal (2,2-dimethyl-1,3-dioxolane-4-methanol).

FIG. 1 shows the percentages w/w of the following fractions, where:

fraction a—corresponds to a light phase of the liquid layer;
fraction b—corresponds to a heavy phase of the liquid layer;
fraction c—corresponds to a bottom layer of decanted salt.

It can be seen that below the molar ratio 4:1, there is no layer c of decanted chloride salt, as it remains solubilized in the liquid medium. Only above molar ratio 4:1 and up to 12:1 the chloride salt becomes insoluble and decants at the bottom of the vessel.

Tables 1 and 2 below show the contents (% w/w) of the indicated compounds, according to specific acetone:glycerol molar ratios.

TABLE 1 light phase (fraction a)

| Molar ratio | glycerol | acetone | dioxolane | water | NaCl |
|---|---|---|---|---|---|
| 1 | 7.11 | 51.2 | 35 | 4.9 | 0.55 |
| 2 | 3.61 | 58.9 | 30.8 | 4.9 | 0.38 |
| 4 | 6.3 | 62.4 | 24.1 | 5.2 | 0.33 |
| 8 | 3.3 | 71.7 | 18.9 | 4.7 | 0.12 |
| 12 | 1.9 | 78.7 | 13.7 | 4 | 0.05 |

TABLE 2 heavy phase (fraction b)

| Molar ratio | glycerol | acetone | dioxolane | water |
|---|---|---|---|---|
| 1 | 54.3 | 14.1 | 12.9 | 12.4 |
| 2 | 53.1 | 14.1 | 10 | 14.3 |
| 4 | 51.1 | 15.8 | 8.2 | 16.1 |
| 8 | 0 | 0 | 0 | 0 |
| 12 | 0 | 0 | 0 | 0 |

It can be seen that as the acetone:glycerol molar ratio increases, the heavy phase decreases and disappears, while (as shown in FIG. 1) the sodium chloride becomes insoluble and decants.

It is understood that with the aid of the information presented herein, the person skilled in the art may deduce the invention to practice in ways not expressly described, but performing substantially the same functions to reach substantially the same results, those equivalent embodiments being encompassed by the following claims.

The invention claimed is:

1. A process for producing a dioxolane compound, said process comprising the steps of:
a)—in a reaction vessel, reacting a crude glycerol and an aldehyde or a ketone with a molar ratio of aldehyde:glycerol or ketone:glycerol from 3:1 to 20:1,
b)—allowing decantation, then separating solids, the remaining liquid fraction presenting a light phase and a heavy phase;
c)—removing salt from said heavy phase, the remaining portion thereof being optionally returned to the reaction vessel;
d)—subjecting said light phase to distillation to separate the dioxolane compound from said ketone or said aldehyde, being optionally recycled to the reaction vessel; and
e)—subjecting the obtained dioxolane compound from step d) to a further distillation to remove water.

2. The process according to claim 1, wherein said molar ratio of aldehyde:glycerol or ketone:glycerol is from 4:1 to 15:1.

3. The process according to claim 1, wherein said ketone in said reaction is at least one ketone selected from the group consisting of acetone, cyclohexanone, methyl cyclohexanone, methyl cyclopentanone, methyl isobutyl ketone, 4-hydroxy-4-methyl-2-pentanone, 2-butanone, 3-butanone, diisobutyl ketone, 4-methyl-3-penten-2-one, 2-nonanone, 2-pentanone, 3-methyl-2-butanone, and 1-phenylethanone.

4. The process according to claim 1, wherein said aldehyde in said reaction is at least one aldehyde selected from the group consisting of formaldehyde, acetaldehyde, 2-ethylhexanal, and furfuraldehyde.

5. The process according to claim 1, wherein said dioxolane compound is a 2-hydrocarbyl-1,3-dioxolane-4-methanol compound.

6. The process according to claim 1, wherein said salt removing in step c) is carried out by filtration, by centrifugation, or by a combination of filtration and centrifugation.

7. The process according to claim 1, wherein a dehydration of said crude glycerol is performed prior to step a).

8. The process according to claim 1, wherein said distillation in step d) is performed in an atmospheric column with temperatures in the range of from 60° C. to 90° C.

9. The process according to claim 1, wherein said distillation in step e) is performed under vacuum of from $1 \times 10^3$ Pa to $3 \times 10^3$ Pa, and temperatures in the range of from 110° C. to 120° C.

10. The process according to claim 1, wherein a neutralization step with an alkali is performed between steps a) and b), and/or between steps b) and c).

11. The process according to claim 1, wherein said light phase, before step d), is subjected to contact with activated carbon or a silica system, and separation.

12. The process according to claim 1, wherein said crude glycerol comprises from 40% to 95% by weight of glycerol.

13. The process according to claim 1, wherein said crude glycerol comprises from 1% to 15% by weight of chlorides.

14. The process according to claim 13, wherein said reaction is carried out in a reaction medium with said molar ratio to form insoluble chlorides, and wherein said process further comprises withdrawing said insoluble chlorides from said reaction medium by decantation or filtration.

15. The process according to claim 14, comprising decantation of said reaction medium to separate decanted chlorides.

16. The process according to claim 15, wherein said decantation provides a light phase, said light phase containing said dioxolane compound and having a chloride content of from 0.005 to 0.8% by weight.

17. The process according to claim 5, wherein said 2-hydrocarbyl-1,3-dioxolane-4-methanol compound is selected from the group consisting of 2,2-dimethyl-1,3-dioxolane-4-methanol, 2,2-diisobutyl-1,3-dioxolane-4-methanol, 2-isobutyl-2-methyl-1,3-dioxolane-4-methanol, 2-butyl-2-ethyl-1,3-dioxolane-4-methanol, and 2-phenyl-1,3-dioxolane-4-methanol.

18. The process according to claim 1, wherein the molar ratio of aldehyde:glycerol or ketone:glycerol is from 6:1 to 12:1.

* * * * *